(12) United States Patent
Day et al.

(10) Patent No.: US 6,719,962 B2
(45) Date of Patent: *Apr. 13, 2004

(54) CONFECTIONERY COMPOSITIONS

(75) Inventors: Trevor Neil Day, Windsor (GB); Mark Greenwood, Woking (GB); Ross Strand, Bracknell (GB)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/146,698

(22) Filed: May 15, 2002

(65) Prior Publication Data

US 2003/0008062 A1 Jan. 9, 2003

Related U.S. Application Data

(60) Provisional application No. 60/291,167, filed on May 15, 2001.

(51) Int. Cl.$^7$ .............................. A61K 9/68; A61K 7/26
(52) U.S. Cl. ........................... 424/48; 424/58; 424/725; 424/440; 426/3; 426/4; 426/5; 426/6; 426/660
(58) Field of Search .................. 424/48, 58, 725, 424/440; 426/3–6, 660

(56) References Cited

U.S. PATENT DOCUMENTS

| | | |
|---|---|---|
| 3,632,358 A | 1/1972 | Echeandia et al. |
| 3,962,463 A | 6/1976 | Witzel |
| 4,170,632 A | 10/1979 | Wagenknecht |
| 4,486,511 A | 12/1984 | Chen et al. |
| 4,792,453 A | 12/1988 | Reed et al. |
| 4,808,401 A | 2/1989 | Gaffar et al. |
| 4,931,295 A | 6/1990 | Courtright et al. |
| 5,017,385 A | 5/1991 | Wienecke |
| 5,532,004 A | 7/1996 | Bell et al. |
| 5,702,687 A | 12/1997 | Miskewitz |
| 5,912,030 A | 6/1999 | Huzinec et al. |
| 5,958,472 A | 9/1999 | Robinson et al. |

FOREIGN PATENT DOCUMENTS

| | | |
|---|---|---|
| EP | 0017691 B1 | 5/1984 |
| EP | 0309414 A2 | 3/1989 |
| EP | 0502750 A1 | 9/1992 |
| FR | 2748902 A1 | 11/1997 |
| GB | 928758 | 6/1963 |
| GB | 950811 | 2/1964 |
| GB | 1081015 | 8/1967 |
| GB | 2096892 A | 10/1982 |
| WO | WO 99/44436 A1 | 9/1999 |
| WO | WO 01/39606 A1 | 6/2001 |

*Primary Examiner*—Frederick Krass
(74) *Attorney, Agent, or Firm*—Emelyn Deleon Hiland

(57) ABSTRACT

Disclosed are stable, portable, oral care confectionery wherein the confectionery composition has a crunchy texture which acts to reinforce for the consumer the oral care benefit of the product. A crunchy, non-cariogenic oral care confectionery composition comprises:

(i) from about 0.1% to about 50%, by weight of the composition, of an oral care active selected from the group consisting of anti-calculus agents; anti-plaque agents; desensitising agents; oral malodour control agents; H2 antagonists; and mixtures thereof;

(ii) from about 0.1% to about 50%, by weight of the composition, of a solid particulate wherein the solid particulate has a particle size such that is passes through a 2000 μm mesh and is retained by a 100 μm mesh and has an aqueous solubility of at least 1 g per 100 ml at 25° C.; and (iii) greater than about 10%, by weight of the composition, of a confectionery carrier material;

wherein compositions comprising polyphosphate with an average anion chain length of greater than or equal to 4 and having the solid particulate properties of (ii) are excluded.

26 Claims, No Drawings

CONFECTIONERY COMPOSITIONS

CROSS REFERENCE

This application claims priority under Title 35, United States Code 119(e) from Provisional Application Ser. No. 60/291,167, filed May 15, 2001.

FIELD OF THE INVENTION

The present invention relates to confectionery compositions such as breath mints, low boiled candy, hard boiled candy, chewing gum, dissolving gums, lozenges, oral pasta, pressed mints, and the like, comprising an oral care active and a solid particulate with a particle size of from about 100 μm to about 2000 μm. More particularly this invention relates to non-cariogenic or so called "sugar free" confectionery compositions. Even more particularly this invention relates to confectionery compositions wherein the solid particulate imparts the crunchy texture to the composition which is detectable during the first few minutes of mastication and which enhances the consumer perception of the oral care benefits. Compositions of the present invention are suitable for use by humans or animals.

BACKGROUND

Regular brushing, especially with a dentifrice or toothpaste comprising an oral care active can help in the prevention and treatment of a wide range of oral care problems including build up of plaque, calculus, gingivitis, gum disease, oral malodour and the like. However, even regular brushing is not sufficient to remove all of debris and microbes which accumulate in the oral cavity and perpetuate these problems. Furthermore, it is generally the habit of consumers to brush their teeth at the beginning and end of each day, and in less developed regions of the world, consumers brush their teeth even less often. Thus food deposits, which build up as a result of eating throughout the day, are left in the oral cavity for long periods of time resulting in enhance activity of the plaque forming microbes.

There is currently a movement in the oral care industry to encourage consumers to use dental hygiene products throughout the day and to brush their teeth more often. However, this is at best inconvenient and is often not possible. As such significant developmental effort has been focused towards developing oral care products in forms which are portable, which can be used several times a day, particularly after eating and which provide anti-plaque and anti-calculus benefits comparable to those obtained by regular brushing with dentifrice. It is hoped that such a product will improve the oral hygiene of consumers. In addition, such a product would make it easier to provide good oral hygiene to children and pets where it is not always easy to regularly brush the teeth.

Confectionery compositions which are popular with both children and adults alike and which are retained in the oral cavity for substantial periods of time during consumption, would seem to make an ideal product form for a portable oral care product. Furthermore chewing gums have many benefits as a portable oral care form since they remain within the oral cavity for significant periods of time, typically 20 mintues or longer. The art of the development and manufacture of a wide range of confectionery compositions is well known. However, the high sugar content of such confectionery compositions has been recognised as a contributory factor in poor dental health. Developments have been made to produce "sugar free", or non cariogenic, confectionery which retain their organoleptic properties but which do not contribute to the formation of dental plaque. In line with this there has recently been some development of confectionery compositions, particularly chewing gum compositions, which comprise one or more oral care agents with the hope of developing products that are able to treat or prevent one or more of a wide range of oral care conditions. Examples include WO 99/44436 which discloses coated chewing gum compositions which comprise materials with known oral care benefits; EP 309,414 which discloses chewing gum compositions comprising polyphosphate; U.S. Pat. No. 4,808,401 which discloses chewing gum comprising fluoride ion source; U.S. Pat. No. 4,170,632 which discloses chewing gum comprising zinc compounds; and U.S. Pat. No. 5,702,687 which discloses chewing gum comprising alkali metal bicarbonate.

However, it has also been shown that, even when confectionery compositions do deliver satisfactory oral care benefits, the consumers do not always appreciate the benefits due to a lack of noticeable and reinforcing signal. In order to successfully market such products it is therefore not only important to deliver the benefit itself but also optimise the sensory signals to reinforce the benefit for the consumer. More recently it has been appreciated that, as with flavour, the texture of products can be leveraged as an important sensory signal to reinforce various primary gum benefits. As such, textured confectionery has assumed commercial importance. One important texture that has been investigated is that a "crunchy" texture which is dispersed throughout the product and not just in the shell. The preferred "crunch" level is similar to that of granulated sugar ie firm and slightly gritty in nature and which produces a slight cracking noise upon consumption. "Crunchy" chewing gums which are particularly desired are those in which the "crunchy" texture lasts throughout the initial minutes of mastication but which disappears with time such that, long term, the gum assumes a non gritty elastomeric texture. In particular this texture has been found to be particularly useful in reinforcing oral care benefits of a chewing gum.

As such, it would be advantageous to be able to create a confectionery product, including a chewing gum, with oral care benefits, particularly improved cleaning and plaque removal benefits, wherein both immediately, and for the first few minutes of mastication, the consumer is able to experience an overall crunchy texture distributed throughout the gum. Furthermore, it would be advantageous to be able to create such a chewing gum wherein, over time, the crunchiness disappeared leaving no gritty overtone. Finally, it would be advantageous to be able to create a confectionery product wherein the sensory experience, including the texture and flavour, reinforced the oral care benefits of the product.

The inclusion of many types of particles within chewing gum or bubble gum compositions are known in the art. These include the incorporation of freeze dried food stuffs (such as fruits, cereals, nuts, coffee and ice-cream) in U.S. Pat. No. 362,358; coated powder particles such as sugar encapsulated dicalcium phosphates in GB 928,758; protein encapsulated sweeteners in U.S. Pat. No. 4,931,295; and organic encapsulated sodium bicarbonate in U.S. Pat. No. 5,702,687; finely divided powders such as tantalum pentoxide in GB 2,096,892; sugars in GB 1,081,015; and insoluble materials such as zeolites, silicates in U.S. Pat. No. 5,912,030; and polymer/gelatine encapsulated oils and flavours in EP 0,502,750; and U.S. Pat. No. 5,532,004. Whilst these disclosures of the prior art provide useful advances in the inclusion of particulates within a chewing gum confectionery product they do not provide any teaching on how to confer a crunchy profile to the product that lasts during the initial minutes of mastication. The disclosures cited would be insufficient for this objective since the particles themselves are either too small to be detectable or "crunchy", or are insoluble which would result in a long lasting gritty texture, or have insufficient hardness to provide the desired "crunch".

Prior art also exists wherein particulate matter has been incorporated into chewing gum compositions such that the resultant product does have a somewhat "crunchy" texture. For example chewing gums with a "crunchy" exterior coating have been previously disclosed such as the hard sugar coated gums disclosed in U.S. Pat. No. 4,486,511 and U.S. Pat. No. 4,792,453 and gums with surface printed solid particles disclosed in U.S. Pat. No. 3,962,463. Such disclosures are limited to a "crunchy" exterior surface of the gum which does not provide the overall texture sensation that is desired to reinforce oral care benefits, the object of the present invention. Furthermore, confectionery gums wherein sugars (such as isomalt, candy and the like), sometimes in conjunction with freeze dried food stuffs, are distributed throughout the body of the gum for the purpose, at least in part, of providing a "crunchy" texture are also known (FR 2,748,902; GB 950,811; EP 017,691; U.S. Pat. No. 5,958,472). Additionally U.S. Pat. No. 5,017,385 discloses a product, which comprises discrete regions of chewing gum composition in combination with discrete regions of a hardboiled sugar candy composition and pending application PCT/US00/17177 provides limited disclosure on how to incorporate long chain crunchy polyphosphate particles into a chewing gum product. Whilst these disclosures provide useful advances in the conferring of a "crunch" to a chewing gum they are still subject to limitations since for example the crunchy is from a limited source, short lived, or provided by a carigoenic sugar material, or is not dispersed evenly throughout the composition. Furthermore they do not teach the use of "crunch" as a sensory signal to enhance the benefit of any oral care active in a sugar free gum.

Surprisingly, it has now been found that when a confectionery composition is prepared comprising an oral care active and from about 0.1% to about 50% of a solid particulate with a particle size in the range from about 100 $\mu$m to about 2000 $\mu$m and an aqueous solubility of at least 5 g per 100 ml at 25° C.; the product has a "crunchy" profile which is noticed by the user during the first few minutes of mastication and which then disappears leaving no detectable residue. In addition this "crunchy" texture provides a sensory signal, which enhances the consumer experience and reinforces the oral care benefits of the composition. Furthermore, by formulating the product in a wide range of confectionery forms, portable oral care, which provides comparable benefits to frequent brushing, has been developed in a product form which is acceptable to a wide range of consumers and cultures and which is easily administered to pets and children.

It is believed that a detectable "crunch" can be conferred to the compositions by ensuring that each individual particle of the solid particulate has a diameter of between about 100 $\mu$m and about 2000 $\mu$m. In addition, by specifying a minimum desired solubility for the particulate, it is possible to ensure that the particle is sufficiently soluble to slowly disintegrate over time within the oral cavity, leaving no detectable gritty texture within the product. It is believed that this texture is ideal for providing a sensory signal that reinforces the oral care benefits of the product. Finally, by preferably using solid particulate, which has a hardness of greater than 1 on the Mohs hardness scale the "crunch" properties of the solid oral care actives are further optimised. Furthermore it has been surprisingly found that when the confectionery composition comprises less than 10% water the solid particulate does not dissolve during manufacture and storage and hence the "crunchy" texture is retained.

It is an object of the present invention to provide sugar free confectionery composition with an oral care benefit which also has a "crunchy" texture and wherein the "crunchy" texture is detected for the initial minutes of mastication but which then disappears with no remaining gritty residue. It is a further object of this invention that the "crunchy" profile of the chewing gum is designed such that it reinforces for the user the oral care benefit of the product. These, and other objects of this invention, will become apparent in light of the following disclosure.

SUMMARY OF THE INVENTION

The present invention relates to a crunchy, non-cariogenic oral care confectionery composition comprising:

(i) from about 0.01% to about 50%, by weight of the composition, of an oral care active selected from the group consisting of anti-calculus agents; anti-plaque agents; desensitising agents; oral malodour control agents; H2 antagonists; and mixtures thereof;

(ii) from about 0.1% to about 50%, by weight of the composition, of a solid particulate wherein the solid particulate has a particle size such that is passes through a 2000 $\mu$m mesh and is retained by a 100 $\mu$m mesh and has an aqueous solubility of at least 1 g per 100 ml at 25° C.;

(iii) greater than about 10%, by weight of the composition, of a confectionery carrier material; and wherein compositions comprising polyphosphate with an average anion chain length of greater than or equal to 4 and having the solid particulate properties of (ii) are excluded.

DETAILED DESCRIPTION OF THE INVENTION

While the specification concludes with claims, which particularly point out and distinctly claim the invention, it is believed the present invention will be better understood from the following description.

All documents cited are, in relevant part, incorporated herein by reference; the citation of any document is not to be construed as an admission that it is prior art with respect to the present invention.

Herein, "comprising" means that other steps and other ingredients which do not affect the end result can be added. This term encompasses the terms "consisting of" and "consisting essentially of".

All percentages and ratios used herein are by weight of the total composition and all measurements made are at 25° C., unless otherwise designated.

The term "safe and effective amount" as used herein means an amount of a compound, component, or composition sufficient to significantly induce a positive benefit, but low enough to avoid serious side effects, i.e. to provide a reasonable benefit to risk ratio, within the scope of sound medical judgement.

The term "orally active" as used herein means a material that provides either a cosmetic, prophylactic or therapeutic benefit within the oral cavity.

The term "confectionery" as defined herein means a solid, gum, gum-like, or glassy composition optionally having a liquid centre filling and/or optionally coated which comprises greater than about 25% sugar or sugar alcohol. Such compositions usually have a sweet taste. Examples of confectionery products include, but are not limited to, breath mints, low boiled candy, chewing gum, hard boiled candy, coated candy, lozenges, oral pasta, pressed mints, throat drops and the like.

The term "chewing gum" as defined herein means a confectionery composition which is suitable for chewing and which comprises 2% or greater, by weight of the composition, of elastomer.

The term "elastomer" as defined herein means a non-digestible polymeric material, or mixture of materials, such as the materials typically used in chewing gum compositions.

The term "crunchy" as defined herein means that the product has a texture such that has a firm and slightly gritty texture and which produces a slight cracking noise upon consumption. It is preferred that the compositions have a texture of granulated sugar.

The term "surface conditioning" as defined herein means creating a hydrophilic tooth surface immediately after treatment; and maintaining these effects for extended periods of time after use.

Active and other ingredients useful herein may be categorised or described herein by their cosmetic and/or therapeutic benefit or their postulated mode of action. However, it is to be understood that the active and other ingredients useful herein can in some instances provide more than one therapeutic and/or cosmetic benefit or operate via more than one mode of action. Therefore, classifications herein are made for the sake of convenience and are not intended to limit an ingredient to the particularly stated application or applications listed.

The elements of the compositions and methods of the present invention are described in more detail below.

Oral Care Active

Compositions of the present invention comprise an oral care active selected from the group consisting of anti-calculus agents; anti-plaque agents; desensitising agents; oral malodour control agents; H2 antagonists; and mixtures thereof. Preferably the oral care active is selected from the group consisting of anti-calculus agents; the group of anti-plaque agents; fluoride ion source; the group of desensitising agents; oral malodour control agents; more preferably the oral care active is an anti-calculus agent; more preferably the oral care active is polyphosphate. It is not intended that the actives listed in groups below are mutually exclusive and a single active may be included in compositions of the present invention to have several effects. It is highly preferred that the oral care active is a solid.

Compositions of the present invention preferably comprise from about 0.01% to about 50%, more preferably from about 0.1% to about 15%, even more preferably from about 0.25% to about 10%, and most preferably from about 0.5% to about 7%, by weight, of oral care active.

Anti-Calculus Agents:

Anti-calculus agents known for use in dental care products include phosphate, pyrophosphate, polyphosphate, phosphonate, polyphosphonate and mixtures thereof. Pyrophosphates are among the best known for use in dental care products. The pyrophosphate salts useful in the present compositions include the dialkali metal pyrophosphate salts, tetra-alkali metal pyrophosphate salts and mixtures thereof in their unhydrated as well as hydrated forms are the preferred species. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) and mixtures thereof. The pyrophosphate salts are described in more detail in Kirk and Othmer, *Encyclopedia of Chemical Technology*, $3^{rd}$ Edition, Volume 17, Wiley Interscience Publishers (1982).

Polyphosphates are the highly preferred anti-calculus agents. Compositions of the present invention preferably comprise greater than about 1%, preferably from about 1.5% to about 50%, more preferably from about 2% to about 15%, even more preferably from about 3% to about 12%, and most preferably from about 5% to about 10%, by weight, of polyphosphate salt. Polyphosphate is a widely used term, which relates to phosphate anions which have been polymerised by dehydration to form a polymer of the phosphate anion. The polyphosphates can exist as linear or cyclic materials or mixtures thereof. It is preferred that the polyphosphates are linear materials comprising only low levels of cyclic materials. Polyphosphates are also characterised by the average anion chain length of the polymer. For the purposes of this invention the polyphosphates referred to are those with an average anion chain length of 3 or greater. It is preferred that the polyphosphates have an average anion chain length of from about 3 to about 40, preferably of from about 6 to about 30; more preferably of from about 10 to about 25 and even more preferably of from about 18 to about 25, and mixtures thereof. Furthermore polyphosphates exist as salts. It is preferred that the polyphosphate is an alkali metal salt, ammonium salt or mixtures thereof, preferably a sodium or potassium salt or mixtures thereof and more preferably a sodium salt. Polyphosphates with an average anion chain length of greater than four usually occur as glassy materials. As defined herein a "glassy" material is one which is amorphous. Preferred in this invention are the linear "glassy" polyphosphates having the formula:

$$XO(XPO_3)_nX$$

wherein X is sodium, potassium, or hydrogen and n averages greater than or equal to 6 or mixtures thereof. Such polyphosphates are manufactured by FMC Corporation and are commercially known as Sodaphos (n≈6), Hexaphos (n≈13), and Glass H (n≈21). Hexaphos and Glass H are preferred with Glass H being the most preferred polyphosphate. These polyphosphates may be used alone or in combination. A broad range of phosphates and their sources are described in Kirk & Othmer, *Encyclopedia of Chemical Technology*, Fourth Edition, Volume 18, Wiley-Interscience Publishers (1996). If a polyphosphate is used in the compositions of the present invention it is preferred that it has a particle size such that it passes through a 50 μm mesh, preferably a 25 μm mesh and more preferably 10 μm mesh. Polyphosphates such as those described not only have an anti-calculus benefit but they also provide surface conditioning effects to the teeth and other surfaces of the oral cavity. The surface conditioning effects include the effective desorption of portions of undesirable pellicle proteins; creating a hydrophilic tooth surface immediately after treatment; and maintaining these effects for extended periods of time after use. These effects result in a clean feeling, which lasts beyond consumption of the confectionery product itself and further contributes to the consumer experience.

Additional anti-calculus agents include polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict and Sunberg on Apr. 28, 1987; polyepoxysuccinates such as those disclosed in U.S. Pat. No. 4,846,650 issued to Benedict, Bush and Sunberg on Jul. 11, 1989; ethylenediaminetetraacetic acid as disclosed in British Patent No 490,384 date Feb. 15, 1937; nitrilotriacetic acid and related compounds as disclosed in U.S. Pat. No. 3,678,154 issued to Widder and Briner on Jul. 18, 1972; polyphosphonates as disclosed in U.S. Pat. No. 3,737,533 issued to Francis on Jun. 5, 1973; U.S. Pat. No. 3,988,443 issued to Ploger, Schmidt-Dunker and Gloxhuber on Oct. 26, 1976 and U.S. Pat. No. 4,877,603 issued to Degenhardt and Kozikowski on Oct. 31, 1989. Anticalculus phosphates include potassium and sodium pyrophosphates; sodium tripolyphosphate; diphosphonates such as ethane-1-hydroxy-1,1-diphosphonate, 1-azacycloheptane-1,1-diphosphonate, and linear alkyl diphosphonates; linear carboxylic acids; and sodium zinc citrate and other soluble zinc salts.

Anti-Plaque Agents:

Anti-plaque agents include anti-plaque agents and flouride ion sources. Anti-plaque agents are any substances which inhibit the accumulation of bacterial deposits on the surfaces of the oral cavity. Examples include xylitol and other anti-microbial agents.

Fluoride Ion Source:

Application of fluoride ions to dental enamel serves to protect teeth against decay. A wide variety of fluoride ion yielding materials can be employed as sources of soluble fluoride in the present compositions. Examples of suitable fluoride ion yielding materials are found in U.S. Pat. No. 3,535,421, issued Oct. 20, 1970 to Briner et al. and U.S. Pat. No. 3,678,154, issued Jul. 18, 1972 to Widder et al. Preferred fluoride ion sources for use herein include sodium fluoride, potassium fluoride, stannous fluoride, ammonium fluoride and mixtures thereof. Sodium fluoride is particularly preferred. Preferably the present composition provide from about 50 ppm to about 10,000 ppm, more preferably from about 100 ppm to about 3000 ppm of fluoride ions.

Desensitising Agents:

Desensitising agents, or anti-pain agents, can also be present in the oral care compositions or substances of the present invention. Such agents may include, but are not limited to, strontium chloride, potassium nitrate, natural herbs such as gall nut, Asarum, Cubebin, Galanga, scutellaria, Liangmianzhen, Baizhi, etc. Analgesics, including low levels of non-steroidal anti-inflammatory agents, such as ketorolac, flurbinprofen, ibuprofen, naproxen, indomethacin, aspirin, ketoprofen, piroxicam and meclofenamic acid, may also be used as desensitising agents.

Oral Malodour Control Agents:

Oral malodour control agents include a wide variety of materials. The most commonly used are antimicrobial agents can also be present in the oral care compositions or substances of the present invention. Such agents may include, but are not limited to, 5-chloro-2-(2,4-dichlorophenoxy)-phenol, commonly referred to as triclosan, and described in the Merck Index, $11^{th}$ Edition, (1989), pp1529 (entry no 9573) in U.S. Pat. No. 3,506,720, and in European Patent Application No 0,251,591 of Beecham Group, Plc, published Jan. 7, 1988; phthalic acid and its salts including, but not limited to those disclosed in U.S. Pat. No. 4,994,262 published Feb. 19, 1991, preferably magnesium mono-potassium phthalate, chlorhexidine (Merck Index, no 2090); alexidine (Merck Index, no 222); hexetidine (Merck Index, no 4624); sanguinarine (Merck Index, no 8320); benzalkonium chloride (Merck Index, no 1066); salicylanilide (Merck Index, no 8299); domiphen bromide (Merck Index, no 3411); cetylpyridinium chloride (CPC) (Merck Index, no 2024); tetradecylpyridinium chloride (TPC); N-tetradecyl-4-ethylpyridinium chloride (TDEPC); octenifine; delmopinol; octapinol; and other piperidine derivatives; nicin preparations; zinc/stannous ion agents; antibiotics such as augmentin, amoxicilline, tetracycline, doxycycline, minocycline, and metronidazole; and analogues and salts of the above; methyl salicyclate; and mixtures of all of the above.

A second class of materials are the anti-bacterial natural plant extracts. These extracts include extracts obtained from any part of the plant including the leaf, stem, bark, pulp, seed, flesh, juice, root and mixtures thereof. It is preferred that the extract is obtained from the leaf, pulp and seed, more preferably from the leaf or seed. Many different plants, or parts of plants, can be used to provide these extracts including tea, especially green tea, magnolia, gold thread, honeysuckle, grape, bergamot, grapefruit, orange, lemon, tangerine, mandarin, satsuma, clementine, lime, and mixtures thereof; preferably from grape, grapefruit and mixtures thereof. Such extracts comprise a wide variety of biologically active materials. These include anthocyanins, flavanols, hydrolysable tannins, alkaloids, lipids, carbohydrates, simple sugars, protein and amino acids, alcohols, polyphenols, organic acids and mixtures thereof. Essential oils are also known to have anti-bacterial properties. These include thymol, geraniol, carvacrol, hinokitiol, eucalyptol, catechol (particularly 4-allyl catechol) and mixtures thereof. It is preferred that compositions of the present invention comprise from about 0.0001% to about 30%, preferably from about 0.001% to about 15%, more preferably from about 0.01% to about 10%, even more preferably from about 0.1% to about 5% and most preferably from about 0.25% to about 3%, by weight of the composition, of extract.

Compositions of the present invention may optionally comprise zinc phytate in combination with natural extracts. The zinc phytate is believed to enhance the polyphenol breath protection efficacy and increase the stability of the polyphenol extract. Compositions of the present invention preferably comprise from about 0.1% to about 10%, more preferably from about 0.5% to about 5% and most preferably from about 1% to about 3%, by weight of the composition, of zinc phytate.

Metal Cations are also commonly used as anti-bacterial agents. The metal cation can be selected from any monovalent or divalent cation selected from the group consisting of zinc, manganese, copper, iron, cobalt, silver, selenium, tin and vanadium; preferably from the group consisting of zinc, manganese, copper, iron, silver, and tin; more preferably from the group consisting of zinc, copper, silver and tin and most preferably from the group consisting of zinc and tin.

A wide variety of metal cation salts are useful in the present invention. These include so called "water-insoluble salts" which have a solubility of less than about 0.5 g per 100 ml at 25° C. and "water soluble salts" which have a solubility of greater than or equal to about 0.5 g per 100 ml at 25° C. It is also possible to use mixtures of these salts. Such mixtures can have several advantages in the compositions of the present invention since they are likely to have different complexing properties with the polyphosphate anions. In addition they have different release rates in the saliva and can therefore act to provide controlled release profiles. Examples of salts that are suitable for use herein include acetate, ammonium sulphate, bromide, chloride, chromate, citrate, dithionate, fluorosilicate, tartrate, fluoride, formate, iodide, nitrate, phenol sulphate, salicyclate, sulphate, gluconate, succinate, glycerophosphate, lactate and mixtures thereof; preferred are acetate, bromide, chloride, citrate, dithionate, tartrate, fluoride, formate, iodide, nitrate, sulphate, gluconate, succinate, lactate and mixtures thereof; and more preferred are acetate, chloride, citrate, sulphate, gluconate, succinate, lactate and mixtures thereof. If stannous chloride is used it may be advantageous to premix the stannous chloride with sodium gluconate prior to incorporating the salt in the composition since this can help to stabilise the stannous ions.

Incorporating a metal cation into compositions of the present invention, which additionally comprise polyphosphate, has an additional benefit of reducing the astringency of the metal cations within the composition thus improving the taste. In order to maximise this benefit it is preferred that the molar ratio of polyphosphate anion to the total combined level of metal cation should be in the range of from about 10:1 to about 1:1, preferably from about 5:1 to about 1:1, preferably from about 3:1 to about 1:1. As used herein the term "polyphosphate anion" refers to a single anion regardless of chain length. The level of polyphosphate anion should be calculated by assuming that all of the polyphosphate material has the chain length of the average anion chain length of the material as quoted by the manufacturer. Compositions of the present invention preferably comprise from about 0.001% to about 5%, preferably from about 0.01% to about 2%, more preferably from about 0.1% to about 1% and most preferably from about 0.1% to about 0.5%, by weight of the composition, of metal salt comprising the orally active metal cation.

Another class of oral malodour control agents include absorbents. These are used to absorb, adsorb, bind or otherwise complex the volatile oral malodour materials. Examples of such agents include talc, mushroom extract, zeolite, cyclodextrin, silica shell and mixtures thereof. Such materials are preferably used at a level of from about 0.5% to about 10%, preferably from about 1% to about 5%, by weight of the composition.

H-2 Antagonists:

Histamine-2 (H-2) receptor antagonist compounds (H-2 antagonists) may be used in the oral care compositions of the present invention. As used herein, selective H-2 antagonists are compounds that block H-2 receptors, but do not have meaningful activity in blocking histamine-1 (H-1) receptors. Selective H-2 antagonists include those disclosed in U.S. Pat. Nos. 5,294,433 and 5,364,616 Singer et al., issued Mar. 15, 1994 and Nov. 15, 1994 respectively and assigned to Procter & Gamble, wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728 and HB-408. Particularly preferred is cimetidine (SKF-92334), N-cyano-N'-methyl-N"-(2-(((5-methyl-1H-imidazol-4-yl)methyl)thio)ethyl)guanidine:

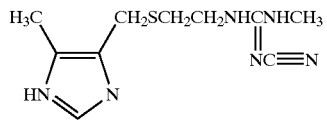

Cimetidine is also disclosed in the Merck Indes, 11$^{th}$ editions (1989), p35$^4$ (entry no 2279), and Physicians' Desk Reference, 46$^{th}$ edition (1992), p2228. Related preferred H-2 antagonists include burimamide and metiamide.

Crunchy Solid Particles

Compositions of the present invention comprise one or more crunchy solid particles dispersed throughout the carrier material. The compositions comprise from about 0.1% to about 50%, preferably from about 0.5% to about 30%, more preferably from about 1% to about 15%, even more preferably from about 5% to abut 12%, by weight of the composition, of solid particulate.

The crunchy particle has a minimum particle size such that the particles are retained by a 0.1 mm mesh, preferably a 0.112 mm mesh, more preferably a 0.16 mm mesh, even more preferably a 0.18 mm mesh and most preferably a 0.2 mm mesh wherein the meshes are selected from the DIN 4188 mesh series. Furthermore the particle preferably has a maximum particle size such that it passes through a 2 mm mesh, preferably a 1 mm mesh, more preferably an 0.8 mm mesh, even more preferably a 0.5 mm mesh and most preferably a 0.4 mm mesh, again wherein the meshes are selected from the DIN 4188 mesh series. The solubility of the particle is preferably at least Ig per 100 ml at 25° C., more preferably at least 5 g, even more preferably at least 8 g and most preferably at least 15 g per 100 ml at 25° C. Thus the solid particulate should be "sparingly soluble", or preferably more soluble, as the term is defined as in the British Pharmacopoeia, 1999, Volume 1. Whilst there is no limit on the upper solubility of the particle it is preferred that it is not "very soluble" in water. Finally it is preferred that the particulate material has a hardness of greater than 1, preferably greater than 2 on the Mohs hardness scale. The particle size, solubility and hardness properties confer a crunchy texture to the confectionery itself.

The weight ratio of confectionery carrier to solid particulate is in the range from about 99:1 to about 1:1, preferably from about 50:1 to about 5:1, more preferably from about 30:1 to about 10:1 and even more preferably from about 25:1 to about 15:1.

Such particles can be present as solid forms of one of the oral care actives outlined above, in the case where the oral care active is a solid, or can be a further particle such as sugar crystals, dried fruits, nuts, etc. However, compositions comprising polyphosphate with a chain length of 4 or greater and wherein the polyphosphate has the properties of the solid particulate are excluded from the scope of this invention.

The solid particulate can comprise singular solid particles or can be a coated encapsulate wherein several primary particles are bound together by an outer material. Singular solid particles are preferred. However, if the particulate is an encapsulate, in order to confer to the final product the desired "crunch" properties it is necessary that the primary particle of the encapsulate has a particle size greater than 100 μm. In addition, the maximum size of an encapsulate should not exceed 2000 μm. Different crunchy textures can be obtained by milling the particles to the desired size or by blending different commercial grades of particles to achieve the desired crunch.

In addition the particulate can comprise less than 10% by weight of the particulate of another material. For example the particulate can be coated in another material such as a sugar, protein and the like. Similarly materials can be adsorbed onto the surface of the solid particulate such as flavours, fragrance, other organic oils and the like. Such additional materials added into the particulate should not alter the properties of the solid such that it no longer has the required oral care benefit, the particle size, solubility or preferred hardness necessary to confer the desired crunch properties to the compositions of the present invention.

The crunchy texture can be used to reinforce the oral care benefits to the consumer. It is preferred that these particles provide a crunchy texture throughout the initial few minutes of mastication but gradually dissolve such that the product does not retain a gritty texture. It is preferred the that crunchy sensation remains consumer noticeable for at least 1 minute 30 seconds, preferably for at least 2 minutes and more preferably for at least 2 minutes 30 seconds. However it is also preferred that the crunchy texture has disappeared by 5 minutes, preferably by 4 minutes so that the material does not abrade the dentin or so that the product does not have a gritty residue.

Water

Compositions of the present invention comprise less than about 10%, preferably less than about 8%, more preferably less than about 5%, even more preferably less than about 3%, and most preferably less than about 2%, by weight of the composition, water. The low levels of water are required in order to ensure that the long chain polyphosphates are not hydrolysed in the final composition.

Water used in the preparation of commercially suitable compositions should preferably be of low ion content and free of organic impurities. The amount of water in a composition should be considered to be not only that added as free water, but also water which is introduced with other materials, such as with sorbitol, silica, surfactant solutions and/or colour solutions. Furthermore the amount of water should be considered by weight of the final composition as a whole including coat and/or filling, where appropriate.

Confectionery Carrier Material

Compositions of the present invention are confectionery compositions including chewing gum. Suitable physical forms include sticks, dragees, chicklets, and batons. Although the exact ingredients for each product form will vary from product to product, the specific techniques will be known by one skilled in the art. However there are some general ingredients which are common to all product forms and these are discussed in more detail below. Preferred product forms are pressed tablets, low boiled candy, hard boiled candy and chewing gum which are readily formulated with less than about 10%, by weight of the composition, water.

Confectionery compositions of the present invention comprise a carrier material. The carrier materials vary depending on the type of confectionery used and would be well known to one skilled in the art. In order that the compositions of the present invention exhibit the desired crunchy properties it is necessary that the composition comprise greater than about 10%, by weight of the composition, of a chewable carrier material. This carrier material can be selected from gums including agar agar gum, gelatine etc; low boiled sugar candy base and gum base materials. It is preferred that the carrier material for compositions of the present invention are not in the form of a whippable or aerated emulsion. Hard and low boiled candy carrier, pressed tablets and the like usually comprise greater than about 70% bulk sweetener including suitable sugar and sugar syrups including cariogenic and non-cariogenic materials. Low boiled candies can also comprise butter to form chewable toffee. For jelly and gum drop compositions the carrier comprises greater than-about 25% bulk sweetener and additionally comprise gums including gum arabic, gelatine, agar agar powder and the like.

Compositions of the present invention are preferably in the form of a chewing gum. As such it is preferred that the compositions comprise greater than about 10%, preferably greater than about 15%, more preferably greater than about 20% and most preferably greater than about 25% up to 75%, by weight of the composition, of gum base. The gum base comprises a carrier material, or mixture of carrier materials, selected from elastomers, resins or waxes. The gum base carrier materials are water insoluble materials which are typically not released in the mouth.

Such materials include:

(i) Elastomers and Elastomer Solvents

Compositions of the present invention preferably comprise an elastomer, or mixture of several different elastomers. Elastomeric materials are generally known in the art but illustrative examples include styrene-butadiene rubber (SBR); synthetic gums; polyisobutylene and isobutylene-isoprene copolymers; natural gums; chicle; natural rubber; jelutong; balata; guttapercha; lechi caspi; sorva; and mixtures thereof. Compositions of the present invention preferably comprise from about 2% to about 30%, more preferably from about 5% to about 25%, by weight, of elastomer. These levels are determined by the desired final texture of the chewing gum since when the total level of elastomer is below about 2% the base composition lacks elasticity, chewing texture, and cohesiveness whereas at levels above about 30% the formulation is hard, rubbery and maintains a tight chew.

Elastomer solvents are also preferably present in compositions of the present invention since they aid softening of the elastomer component. Preferred examples of elastomer solvents for use herein include the pentaerythritol ester of partially hydrogenated wood rosin, pentaerythritol ester of wood rosin, glycerol ester of partially dimerized rosin, glycerol ester of polymerised rosin, glycerol ester of tall oil, wood or gum rosin, glycerol ester of partially hydrogenated rosin, methyl ester of partially hydrogenated rosin, and mixtures thereof. Compositions of the present invention preferably comprise from about 2% to about 50%, more preferably from about 10% to about 35%, by weight, of elastomer solvent.

(ii) Resins and Waxes

Resins are an optional, but desirable, ingredient of chewing gum compositions herein. They serve to plasticise the gum base. Suitable resins include polyvinyl acetate (PVA); terpene resins, including polyterpene and polymers of alpha-pinene or beta-pinene; and mixtures thereof. Such compositions preferably comprise from about 3% to about 25%, preferably from about 5% to about 20%, by weight, of resin.

The chewing gum compositions may also include one or more waxes. Suitable waxes include paraffin wax; microcrystalline wax; Fischer-Tropsch paraffin; natural waxes such as candellilla, carnauba and beeswax; polyolefin waxes such as polyethylene wax; and mixtures thereof. Compositions comprise up to about 25%, preferably from about 5% to about 20%, by weight, of wax.

Confectionery compositions of the present invention can be centre filled. Such products preferably comprise from about 60% to about 95%, more preferably from about 75% to about 85% of an edible shell and from about 5% to about 40%, preferably from about 15% to bout 25%, by weight of the composition, of an edible filling. It is possible that centre filled confectionery composition can comprise an oral care active in the edible shell and or a different oral care active, or mixture of actives, in the edible filling. In addition the composition can comprise different flavouring agents in the shell and the filling.

Furthermore the confectionery compositions of the present invention can also be coated. The outer coating may be hard or crunchy. Typically, the outer coating will essentially consist of sorbitol, maltitol, xylitol, isomalt, and other crystallisable polyols. Furthermore the coating will typically consist of several opaque layers, such that the confectionery core is not visible through the coating itself, which can optionally be covered with a further one or more transparent layers for aesthetic, textural and protective purposes. The outer coating may also contain small amounts of water and gum arabic. A polyol coating can be further coated with wax. The coating is applied in a conventional manner by successive applications of a coating solution, with drying in between each coat, as described in WO99/44436. As the coating dries it usually becomes opaque and is usually white, though other colorants may be added. A polyol coating can be further coated with wax. The coating can further comprise coloured flakes or speckles. If the composition comprises a coat it is possible that one or more of the oral care actives can be dispersed throughout the coat. This is especially preferred if one or more oral care active is incompatible in a single phase composition with another of the actives.

Balance of the Composition

Compositions of the present invention preferably comprise safe and effective levels of one or more additional components. Such materials are well known and are readily chosen by one skilled in the art based on the oral care, physical and aesthetic properties desired for the compositions being prepared. Examples of such materials include, but are not limited to fats, solvents, waxes, emulsifiers, softeners, bulking agents, cationic material, buffers, whitening agents, alkali metal bicarbonate salts, thickening materials, humectants, water, surfactants, titanium dioxide, flavouring agents, colouring agents, and mixtures thereof. Those ingredients most commonly used are described in more detail below.

Antioxidants

Antioxidants are generally recognised as useful in compositions such as those of the present invention. Antioxidants are disclosed in texts such as Cadenas and Packer, The Handbook of Antioxidants, ©1996 by Marel Dekker, Inc. Antioxidants that may be included in the oral care compositions of the present invention include, but are not limited to, Vitamin E, ascorbic acid, Uric acid, carotenoids, Vitamin A, flavenoids and polyphenols, herbal antioxidants, melatonin, aminoindoles, lipoic acids and mixtures thereof.

Teeth Colour Modifying Substances

Teeth colour modifying substances may be considered among the oral care actives useful in the present invention. These substance are suitable for modifying the colour of the teeth to satisfy the consumer such as those listed in the CTFA Cosmetic Ingredient Handbook, $3^{rd}$ Edition, Cosmetic and Fragrances Association Inc., Washington D.C. (1982), incorporated herein by reference. Specific examples include talc, mica, magnesium carbonate, calcium carbonate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical pigment levels from about 0.05% to about 20%, preferably from about 0.1% to about 15% and most preferably from about 0.25% to about 10%, by weight, of the composition.

Compositions for use herein may also comprise materials that remove or bleach intrinsic or extrinsic stains on or in tooth surfaces. Such substance are selected from the group consisting of the peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. Additional bleaching substances may be hypochlorite, and chlorine dioxide. A preferred percarbonate is sodium percarbonate. Preferred persulphates are oxones. The level of these substances is dependent on the available oxygen or chlorine. This level is generally used in compositions of the present invention at levels from about 0.1% to about 35%, preferably from about 1% to about 25% and most preferably from about 5% to about 10%, by weight of the composition.

Nutrients

Nutrients may improve the condition of the oral cavity and can be included in the oral care compositions or substances of the present invention. Nutrients include minerals, vitamins, oral nutritional supplements, enteral nutritional supplements, herbal supplements, natural extracts and mixtures thereof as disclosed in Drug Facts and Comparisons (loose leaf drug information service), Wolters Kluer Company, St Louis, Mo., ©1997. Minerals that can be included with the compositions of the present invention include calcium, phosphorus, fluoride, zinc, manganese, potassium and mixtures thereof. Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Fish oil contains large amounts of Omega-3 (N-3) polyunsaturated fatty acids, eicosapentaenoic acid and docosahexaenoic acid.

Non Cariogenic Sweeteners

Two main types of sweeteners exist; bulk sweeteners and high intensity sweeteners. In general, the amount of sweetener used will vary depending on the sweetener and the overall desired aesthetics but levels used should be high enough such that the desired level of sweetness is achieved independent from the flavour. When bulk sweeteners are used they can also assume the role of the bulking agent or filler within the composition.

Bulk Non Cariogenic Sweeteners:

Compositions of the present invention preferably comprise a non-cariogenic sweetener. As used herein the term "non-cariogenic" refers to sweeteners which are not able to be metabolised by oral microbes and therefore do not contribute to the formation of dental caries. It is preferred that compositions of the present invention comprise greater than about 10%, preferably greater than about 20%, more preferably greater than about 30% and most preferably greater than about 40%, by weight of the composition, of non cariogenic sweetener. Compositions of the present invention may comprise up to about 99%, by weight of the composition, non cariogenic sweetener.

Preferred bulk non cariogenic sweetening agents are sugar alcohols such as sorbitol, xylitol, mannitol, maltitol, isomalt, hydrogenated starch hydrolisate, insulin, and other non-carigenic edible polyols such as glycerin and erythritol and mixtures thereof. Most preferred are non cariogenic sweeteners selected from the group consisting of maltitol, mannitol, xylitol, sorbitol, sucralose, aspartame and its salts, and mixtures thereof. In general compositions comprise from about 10% to about 80%, more preferably from about 30% to about 70%, by weight, of bulk sweetener.

High Intensity Sweeteners:

High intensity sweeteners are preferred over bulk sweeteners for use in compositions of the present invention because, for among other reasons, high intensity sweeteners may prolong the flavour of the finished gum composition during chewing. Suitable high intensity sweeteners include: dipeptide based sweeteners such as L-aspartyl-L-phenylalanine methyl ester (Aspartame) and equivalents (described in U.S. Pat. No. 3,492,131), L-α-aspartyl-N-(2, 2,4,4-tetramethyl-3-thietanyl)-D-alaninamide hydrate (Alitame) and the like; saccharin and its soluble salts eg sodium or calcium saccharin salts; cyclamate salts for example acesulfame-K and the like; chlorinated derivatives of sucrose such as chlorodeoxysucrose and the like; and protein based sweeteners, such as Thaumatin (talin). Compositions of the present invention preferably comprise from about 0.01% to about 2.0%, more preferably from about 0.05% to about 0.5%, by weight, of high intensity sweetener.

Additional Chewing Gum Ingredients

There are several ingredients which are commonly added to chewing gum compositions and which are not commonly used in other types of confectionery. Examples of materials are listed below but this list is not to be considered limiting. Similarly such ingredients can be used in other types of confectionery if desired.

Chewing gum compositions of the present invention may also comprise plasticisers in addition to the resin component. Suitable plasticisers include glyceryl triacetate, acetylated monoglyceride, glyceryl tributyrate, ethyl laurate, ethyl acetoacetate, diethyl tartrate, ethyl or butyl lactates, diethyl malate, ethyl oleate, castor oil, succinylated monoglycerides or mixtures thereof. Glyceryl triacetate and acetylated monoglyceride are preferred. Compositions preferably comprise up to about 10%, preferably from about 0.1% to about 3%, by weight, of plasticiser.

Compositions of the present invention preferably comprise a softener or mixture of softeners which, when incorporated into the gum base, assist in modifying the texture and consistency properties. In particular, they help to soften the chew and to maintain chew softness over an extended period of time. Suitable softeners include fatty materials such as lanolin, stearic acid, sodium stearate and potassium stearate; polyhydric alcohols such as glycerine, propylene glycol, and the like; and mixtures thereof. Compositions preferably comprise up to about 30%, more preferably from about 0.1% to about 10%, by weight, of softener. In a preferred embodiment, the chewing gum composition comprises from about 0.1% to about 10%, by weight, of a fatty softener selected from stearic acid, sodium stearate, potassium stearate and mixtures thereof, preferably stearic acid.

The chewing gum compositions preferably comprise an emulsifier such as glycerol monostearate, lecithin, fatty acid monoglycerides, diglycerides, propylene glycol monostearate and mixtures thereof. Compositions comprise up to about 10%, and preferably from about 2% to about 6%, by weight, of emulsifier.

Various fats can also be included in the chewing gum compositions of the present invention. Preferred fats include the hydrogenated vegetable oils such as hydrogenated palm oil, hydrogenated soybean oil, hydrogenated cotton seed oil and various other hydrogenated vegetable oils and mixtures thereof. The fats can suitably be used at a level up to about 20%, preferably from about 1% to about 10%, by weight, of the chewing gum composition.

Bulking Agents

Bulking agents, such as fillers, can also be employed in confectionery. Suitable fillers and bulking agents are generally non-abrasive, preferably with an average particle size less than 5 $\mu$m, more preferably less than 3 $\mu$m and especially less than 1 $\mu$m. Illustrative bulking agents include calcium carbonate or ground limestone, talc, aluminium hydroxide, alumina, aluminium silicates, dicalcium phosphate and mixtures thereof. Compositions preferably comprise up to about 50%, more preferably up to about 30%, and most preferably up to about 10%, by weight, of bulking agent.

Flavouring Agents

Compositions of the present invention can preferably comprise a flavouring agent. As used herein the term "flavouring agent" means those flavour essences and equivalent synthetic materials, which are added to flavour the composition. The flavouring agent can also include specific materials, which are added to provide a warming or cooling sensation.

Flavouring agents are well known in the art. They include synthetic flavours and or oils and or essences derived from plants, roots, beans, nuts, leaves, flowers, fruits and so forth and mixtures thereof. Examples of suitable flavours include lemon, orange, banana, grape, lime, apricot, grapefruit, apple, strawberry, cherry, chocolate, pineapple, coffee, cocoa, cola, peanut; almond, liquorice, cinnamon and the like. The amount of flavouring agent employed is normally a matter of preference but in general they are used in amounts up to about 4%, preferably from about 0.1 to about 1%, by weight of the composition.

Compositions of the present invention can optionally comprise a cooling agent and suitable materials are described in WO 97/06695. Preferred for use herein are physiological cooling agents selected from the group consisting of menthol, peppermint oil, N-substituted-p-menthane-3-carboxamides, acyclic tertiary and secondary carboxamides, 3-1-methoxy propan-1,2-diol and mixtures thereof. Particularly preferred are menthol and menthol containing oils such as peppermint oil. Cooling agents are preferably used at a level of from about 0.001 to about 5%, more preferably from about 0.05% to about 3.5%, by weight of the composition.

Compositions of the present invention can optionally comprise a warming agent. Preferred agents include those selected from the group consisting of vanillyl alcohol n-butyl ether, vanillyl alcohol n-propyl ether, vanillyl alcohol n-butyl ether, vanillyl alcohol isobutyl ether, vanillyl alcohol n-amino ether, vanillyl alcohol isamyl ether, vanillyl alcohol n-hexyl ether, vanillyl alcohol methyl ether, vanillyl alcohol ethyl ether, ginerol, shogaol, paradol, zingerone, capsaicin, dihydrocapsaicin, nodihydrocapsaicin, homocapsaicin, homodihydrocapsaicin, ethanol, isopropyl alcohol, iso-amylalcohol, benzyl alcohol, chloroform, eugenol, cinnamon oil, cinnamic aldehyde, and mixtures thereof. Warming agents are preferably used at a level of from about 0.001 to about 5%, more preferably from about 0.05% to about 3.5%, by weight of the composition.

Preparation of Compositions

The compositions of the present invention are prepared by standard techniques well known to those skilled in the art. If the composition comprises more than one phase, in general the different phases will be prepared separately, with materials of similar phase partitioning being added in any order. The two phases will then be combined with vigorous stirring to form the multiphase system eg an emulsion or dispersion. Any ingredients in the formulation with high volatility, or which are susceptible to hydrolysis at high temperatures, will usually be added post mixing of the different phases with gentle stirring. If the composition optionally comprises polyphosphate it is preferred that the polyphosphate is not pre-dispersed in water prior to addition to the composition in order to prevent hydrolysis. Typical confectionery methods are highly suitable for manufacturing of compositions of the present invention. Finally if the products are coated the coating step is conducted as a final step. The coating can be applied by panning or spray dried techniques commonly known to those skilled in the art.

EXAMPLES

The following examples further illustrate the preferred embodiments within the scope of the present invention. These examples are given solely for the purpose of illustration and are not to be construed as limitations of the present invention as many variations of the invention are possible without departing from its spirit or scope. Unless otherwise indicated, all ingredients are expressed as a weight percentage of the composition.

| INGREDIENT | I % w/w | II % w/w | III % w/w | IV % w/w | V % w/w |
|---|---|---|---|---|---|
| Gumbase | 32.00 | 32.00 | 30.00 | 30.00 | 28.00 |
| Sorbitol | 58.00 | 58.44 | 55.45 | 57.20 | 42.95 |
| Xylitol | — | — | — | — | 20.00 |
| Glycerin | 5.00 | 5.00 | 5.00 | 5.00 | 5.00 |
| Water | 1.00 | 1.00 | 1.00 | 1.00 | 1.00 |
| Tin Chloride | — | 0.01 | — | — | — |
| Zinc Acetate | 0.45 | — | — | — | 0.50 |
| Grapefruit Seed Extract | — | — | 1.00 | — | — |
| Eucalyptol | — | — | — | 0.25 | — |
| Calcium lactate*** | — | 1.00 | — | — | — |
| Sodium tripolyphosphate** | 1.00 | — | — | — | — |
| Sodium Bicarbonate*** | — | — | — | 4.00 | — |
| Sodium polyphosphate* (n = 21) | — | — | 5.00 | — | — |
| Flavour | 2.50 | 2.50 | 2.50 | 2.50 | 2.50 |
| Acesulfam K | 0.05 | 0.05 | 0.05 | 0.05 | 0.05 |
| TOTAL | 100.00 | 100.00 | 100.00 | 100.00 | 100.00 |
| COATING (20–30% w/w) | | | | | |
| Sorbitol | — | — | — | — | 94.80 |
| Water | — | — | — | — | 2.00 |
| Titanium Dioxide | — | — | — | — | 1.50 |
| Acesulfam K | — | — | — | — | 0.05 |
| Polysorbate 60 | — | — | — | — | 0.15 |
| Flavour | — | — | — | — | 1.50 |
| TOTAL | — | — | — | — | 100.00 |

*Sodium polyphosphate (n = 21): Milled grade; median particle size < 50 μm
**Sodium tripolyphosphate: Median particle size > 100 μm
***Sodium Bicarbonate, Calcium lactate, potassium citrate: Median particle size > 100 μm Examples 1–5

Chewing gums: Melt gumbase to 55–60° C. in sigma blade mixer. Add in bulk sweetener and glycerin, mix. Add in active and mix. Mix in flavour last. Remove from heat and allow to cool before moulding and cutting. Coating presolution is sprayed onto cooled gum in fine layers which are allowed to dry before subsequent layers are added. Sufficient coating is added such that total coating weight is 20–30% of final finished pellet weight.

| INGREDIENT | VI % w/w | VII % w/w | VIII % w/w | IX % w/w | X % w/w |
|---|---|---|---|---|---|
| Gumbase | 32.00 | 32.00 | 32.00 | — | — |
| Sorbitol | 55.40 | 57.05 | 57.95 | — | — |
| Isomalt | — | — | — | 86.62 | 85.62 |
| Glycerin | 5.00 | 5.00 | 5.00 | — | — |
| Gelatine | — | — | — | 0.10 | 0.10 |
| Gum arabic | — | — | — | 0.10 | 0.10 |
| Vegetable Fat | — | — | — | 5.00 | 5.00 |
| Water | 1.00 | 1.00 | 1.00 | 6.00 | 6.00 |
| Tin Chloride | 0.05 | — | — | 0.03 | 0.03 |
| Grapefruit Seed Extract | — | — | 0.50 | — | — |
| Eucalyptol | — | 0.40 | — | — | — |
| Potassium Citrate*** | — | 2.00 | 1.00 | — | 2.00 |
| Calcium lactate*** | — | — | — | 1.00 | — |
| Sodium Bicarbonate*** | 4.00 | — | — | — | — |
| Flavour | 2.50 | 2.50 | 2.50 | 1.00 | 1.00 |
| Lecithin | — | — | — | 0.10 | 0.10 |
| Acesulfam K | 0.05 | 0.05 | 0.05 | 0.05 | 0.05 |
| TOTAL | 100.00 | 100.00 | 100.00 | 100.00 | 100.00 |

***Sodium Bicarbonate, Calcium lactate, potassium citrate: Median particle size > 100 μm Examples 6–8

Chewing gums: Melt gumbase to 55–60° C. in sigma blade mixer. Add in bulk sweetener and glycerin, mix. Add in active and mix. Mix in flavour last. Remove from heat and allow to cool before moulding and cutting. Coating presolution is sprayed onto cooled gum in fine layers which are allowed to dry before subsequent layers are added. Sufficient coating is added such that total coating weight is 20–30% of final finished pellet weight.

Examples 9, 10

Low boiled candy: Isomalt is slowly dissolved in water to 80° C. and subsequently cooked to 118–130° C. at which point the heating is removed. Butter or other fat is added 2–3° C. lower than this final cook temperature. Gelatine, flavours, acid and actives are added after cooking has ended following which the final products are formed.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A crunchy, non-cariogenic oral care confectionery composition comprising:
   (i) from about 0.01% to about 50%, by weight of the composition, of an oral care active selected from the group consisting of anti-calculus agents; anti-plaque agents; desensitizing agents: oral malodour control agents; H2 antagonists; and mixtures thereof;
   (ii) from about 0.1% to about 50%, by weight of the composition, of a solid, sparingly soluble and crunchiness conferring particulate wherein the solid particulate has a particle size such that is passes through a 2000 μm mesh and is retained by a 100 μm mesh and has an aqueous solubility of at least 1 g per 100 ml at 25° C., said crunchiness disappearing after the initial minutes of mastication leaving substantially no gritty residue; and (iii) greater than about 10%, by weight of the composition, of chewing gum base as a confectionery carrier material;

wherein the confectionery composition has an outer coating but excluding compositions comprising a polyphosphate with an average anion chain length of greater than or equal to 4 and having said solid particulate properties of (ii).

2. A composition according to claim 1 wherein the composition comprises from about from about 0.1% to about 50% of oral care active by weight of the composition.

3. A composition according to claim 1 or claim 2 wherein the oral care active is a solid.

4. A composition according to claim 1 wherein the oral care active is selected from the group consisting of a polyphosphate, pyrophosphate, phosphonate, zinc salts, tin salts, calcium salts and mixtures thereof.

5. A composition according to claim 4 wherein the polyphosphate has an average anion chain length of from about 3 to about 40.

6. A composition according to claim 4 wherein the polyphosphate has an average anion chain length of from about 18 to about 25.

7. A composition according to of claim 4 wherein the polyphosphate is an alkali metal or ammonium salt.

8. A composition according to claim 5 wherein the polyphosphate has a particle size such that it passes through a 50 μm mesh.

9. A composition according to claim 1 wherein the solid particulate has a particle size such that it passes through a 1000 μm mesh.

10. A composition according to claim 1 wherein the solid particulate has a particle size such that it passes through a 850 μm mesh.

11. A composition according to claim 1 wherein the solid particulate has a particle size such chat it passes through a 500 μm mesh.

12. A composition according to claim 1 wherein the solid particulate has a particle size such that it passes through a 400 μm mesh.

13. A composition according to claim 1 wherein the solid particulate has a particle size such that it is retained by a 105 μm mesh.

14. A composition according to claim 1 wherein the solid particulate has a particle size such that it is retained by a 150 μm mesh.

15. A composition according to claim 1 wherein the solid particulate has a particle size such that it is retained by a 175 μm mesh.

16. A composition according to claim 1 wherein the solid particulate has a particle size such that it is retained by a 200 μm mesh.

17. A composition according to of claim 1 wherein the solid particulate has an aqueous solubility of at least 5 g per 100 ml at 25° C.

18. A composition according to claim 1 wherein the solid particulate has a hardness of greeter than 1, when measured using the Mobs hardness scale.

19. A composition according to claim 1 wherein the composition comprises from about 0.5% to about 30% of solid particulate by weight of the composition.

20. A composition according to claim 19 wherein the composition comprises from about 5% to about 12% of solid particulate by weight of the composition.

21. A composition according to claim 1 wherein the oral care active has the properties of the solid particulate unless the oral care active is a polyphosphate with an average anion chain length of greater than or equal to 4.

22. A composition according to claim 1 wherein the composition comprises greater than about 20% of gum base by weight of the composition.

23. A composition according to claim 1 wherein the composition comprises less than about 8% water by weight of the composition.

24. A composition according to claim 23 wherein the composition comprises less than about 2% water by weight of the composition.

25. A composition according to claim 1 wherein the composition comprises greater than about 10% of non-cariogenic sweetener by weight of the composition.

26. A composition according to claim 1 wherein the weight ratio of confectionery carrier to solid particulate is in the range from about 99:1 to about 1:1.

* * * * *

UNITED STATES PATENT AND TRADEMARK OFFICE
CERTIFICATE OF CORRECTION

PATENT NO. : 6,719,962 B2
APPLICATION NO. : 10/146698
DATED : April 13, 2004
INVENTOR(S) : Trevor Neil Day et al.

It is certified that error appears in the above-identified patent and that said Letters Patent is hereby corrected as shown below:

<u>Column 9</u>
Line 65, delete p35$^4$ and insert p354.

<u>Column 16</u>
Line 21, delete -- ; -- and insert -- , --.

Signed and Sealed this

Twenty-second Day of August, 2006

JON W. DUDAS
*Director of the United States Patent and Trademark Office*